United States Patent [19]

Abdrakhmanov et al.

[11] Patent Number: 5,119,661
[45] Date of Patent: Jun. 9, 1992

[54] APPARATUS FOR MANUFACTURING PROFILE PIPES USED IN WELL CONSTRUCTION

[76] Inventors: Gabdrashit S. Abdrakhmanov, ulitsa Gogolya, 66, kv. 71; Albert G. Zainullin, ulitsa Saidasheva, 1, kv. 117, both of Bugulma; Anatoly V. Perov, Varshavskoe shosse, 143, korpus 1, kv. 89; Rishad T. Bulgakov, ulitsa Akademika Piljugina, 8, korpus 1, kv. 38, both of Moscow; Yaroslav V. Vakula, ulitsa Lenina, 16, kv. 14, Tataraskaya ASSR, Almetievsk; Alexandr A. Fotov, ulitsa Sovetskoi Armii, 7, kv. 25, Moscow; Veniamin N. Duev, ulitsa Vatutina, 42, kv. 22, Sverdlovskaya oblast, Pervouralsk; Gennady P. Moiseev, ulitsa Pervomaya, 11, kv. 45, Sverdlovskaya oblast, Pervouralsk; Ivan A. Lyashenko, ulitsa Kosmonavtov, 17b, kv. 12, Sverdlovskaya oblast, Pervouralsk; Shamil K. Shayakhmetov, ulitsa Gafiatullina, 16, kv. 6; Rustam K. Ibatullin, ulitsa Gogolya, 66, kv. 49, both of Bugulma; Vladimir A. Aleshin, ulitsa 1 Maya, 8a, kv. 7; Alexandr Y. Frolov, prospekt Iliicha, 12, kv. 7, both of Sverdlovskaya oblast, Pervouralsk; Ilmas F. Mingazov, ulitsa Vakhitova, 4, kv. 36, Bugulma; Ildus Z. Vafin, ulitsa Zavòdskaya, 24, kv. 2, Tatarskaya ASSR, rabochy poselok Shugurovo, all of U.S.S.R.

[21] Appl. No.: 543,791
[22] PCT Filed: Nov. 22, 1988
[86] PCT No.: PCT/SU88/00239
  § 371 Date: Jul. 20, 1990
  § 102(e) Date: Jul. 20, 1990
[87] PCT Pub. No.: WO90/05598
  PCT Pub. Date: May 31, 1990
[51] Int. Cl.$^5$ .......................... B21C 1/04; B21C 3/08
[52] U.S. Cl. ......................................... 72/276; 72/278
[58] Field of Search ............... 72/206, 274, 278, 282, 72/290, 450, 451, 276, 283, 370; 166/77, 277

[56] References Cited

U.S. PATENT DOCUMENTS

| 541,053 | 6/1895 | Peirce | 72/367 |
|---|---|---|---|
| 3,487,673 | 1/1970 | House | 72/282 |
| 4,079,616 | 3/1978 | Zazimko et al. | 72/278 |
| 4,879,892 | 11/1989 | Paraskevas | 72/290 |

FOREIGN PATENT DOCUMENTS

| 10823 | 7/1929 | U.S.S.R. | |
| 198987 | 6/1967 | U.S.S.R. | 72/274 |
| 314570 | 9/1971 | U.S.S.R. | 72/276 |
| 425689 | 4/1974 | U.S.S.R. | |
| 549196 | 3/1977 | U.S.S.R. | |
| 827208 | 5/1981 | U.S.S.R. | 72/278 |
| 860913 | 9/1981 | U.S.S.R. | 72/276 |
| 997892 | 2/1983 | U.S.S.R. | 72/276 |

OTHER PUBLICATIONS

A. K. Shurupov, M. A. Freiberg, "Proizvodstvo truboekenomichnykh profiley"/Production of Economical Profile Pipes/, Gosudarstvennoye nauchbno-tekinicheskoye izdatel'stvo po chernoi i tsvetno metallurgill/Sverdlovsk/, p. 146.

*Primary Examiner*—Lowell A. Larson
*Assistant Examiner*—Thomas C. Schoeffler
*Attorney, Agent, or Firm*—Fleit, Jacobson, Cohn, Price, Holman & Stern

[57] ABSTRACT

The method resides in profiling a part of a cylindrical pipe by drawing it through a moulding device, and reducing the pipe over its entire length for the diameter of the cylindrical part of the pipe to be substantially equal to the diameter of the circumscribed circle of its profiled part.

The apparatus for performing the method comprises a drawing bench supporting a drawing die (2) accommodated in a housing (1) and a drawing carriage. Cams (6) are situated in front of the drawing die (2) at both sides of the path of the travel of a pipe (5) being manufactured, their one ends carrying deforming rollers (7) and their other ends carrying forked levers (8) cooperating with the drawing carriage through a tie (11) with slots (10) receiving therein lock pins (9) adapted to engage the forked levers (8). The apparatus further includes a pivoted lever (29) with a bearing roller (31), mounted on the housing (1). One arm of the pivoted lever (29) is adapted to engage the pipe (5) being profiled through the bearing roller (31), and the other arm thereof carries pivotally mounted stops (26) adapted for periodical cooperation with the cams (6).

2 Claims, 3 Drawing Sheets

APPARATUS FOR MANUFACTURING PROFILE PIPES USED IN WELL CONSTRUCTION

TECHNICAL FIELD

The present invention relates to working of metals by application of pressure, and more particularly it relates to a method of manufacturing profile pipes of the kind used in oil and gas well construction, and to an apparatus capable of performing this method.

The present invention can be employed to the utmost effect in the production of profile pipes used for patching off troublesome zones in well-drilling.

PRIOR ART

It frequently occurs in the drilling of deep wells that some of the exposed rock formations either intensely absorb the drilling mud or discharge their own formation fluid into the borehole. When such formations are being isolated by conventional cementing techniques, more often than not this fails to produce the desired results. The approaches used nowadays in such cases involve setting pre-reeled holder-type metal patchers, or else intermediate pipe strings—either complete (i.e. starting at the well head) or curtailed.

However, patchers have failed to find broad fields of application on account of their not ensuring adequate fluid-tightness in isolating a troublesome zone; besides, they cannot be made of relatively great lengths, so that they are not suitable for high-effect isolation of troublesome zones whose extent is several tens or even hundreds of meters.

When intermediate pipe strings, whether complete or curtailed, are used for the purpose, the troublesome zones are reliably patched off. However, the operations involved incur considerable costs of cementing such strings in the well and of the excessive input of the metal, cement and time. Furthermore, with every new intermediate string installed in the well, the well diameter becomes smaller, which adversely affects the production conditions.

There is known a method of manufacturing profile pipes including the operation of profiling the central portion of a cylindrical pipe by drawing it through a moulding device (SU, A, 549196).

The apparatus capable of performing this method comprises a drawing die including a sleeve with a shaped die made of split shaping elements mounted on resilient rods interconnected by a ring, and a unit for applying an external load to the shaped die. The resilient members are interconnected at a distance from the end face of the die, which is not shorter than two lengths of the shaping elements of the die.

A major drawback of the abovedescribed known method and of the apparatus for performing this method is that profile pipes thus produced would not be run into a well and set in a troublesome zone with tight engagement with the borehole wall, because this requires that the pipe stock (blank) prior to its profiling should have an outer diameter equalling the borehole or well diameter in the troublesome zone.

However, when pipes are profiled in accordance with the above method of the prior art, the pipe has its diameter reduced only over its central shaped portion, the cylindrical ends of the pipe retaining the initial diameter and, hence, would not be run into a well. If the diameter of the pipe is reduced still further, the pipe would not be properly set in a troublesome zone in a well, as its wall would fail to engage the borehole wall. The above drawback becomes even more marked when the patching-off of troublesome zones is conducted with expanding the diameter of the borehole in the troublesome zone beyond the well diameter, so as not to reduce the flow passage of the well.

Another shortcoming of the known method and apparatus for performing it is the process of producing a profile pipe with two cylindrical ends being performed in a succession of steps, which both complicates the manufacture of such pipes and makes them costly, to say nothing of the adversely affected productivity.

There is further known a method of manufacturing profile pipes by drawing them through a moulding device (A. K. Shurupov, M. A. Freiberg, "Proizvodstvo truboekenomichnykh profiley" /Production of Economical Profile Pipes/, Gosudarstvennoye nauchno-teknicheskoye izdatel'stvo po chernoi i tsvetnoi metallurgii /Sverdlovsk/, p. 146). According to this method, the required profile of the pipe is maintained the same throughout its length.

A drawback of this technology is that pipes manufactured in the above process are joined into a string by having their ends welded together, which is quite complicated under the field conditions of well drilling. Furthermore, their running-in and setting in a well involves the use of such sophisticated devices as a special-design collet head and a burnishing (expanding) head.

It is an object of the present invention to create a method of manufacturing pipes with cylindrical ends, which should be suitable for patching off troublesome zones in a well without reducing the flow passage diameter thereof.

It is another object of the present invention to simplify the technology of manufacturing profile pipes, and to make it less costly.

It is one more object of the present invention to step up the productivity of profile pipe manufacture.

The main object of the present invention is to create a method of manufacturing profile pipes used in well construction and an apparatus for performing this method, which should provide for producing a profile pipe with a cylindrical portion having its diameter substantially equal to the diameter of the circumscribed circle of the shaped portion of the pipe.

DISCLOSURE OF THE INVENTION

This object is attained in a method of manufacturing profile pipes used in well construction, residing in drawing cylindrical pipes through a moulding device, in which method, in accordance with the present invention, the profiling of each pipe is performed over only a part of its length, the method including the reducing of the pipe diameter throughout its entire length, with the aim of making the diameter of the non-profiled cylindrical portion of the pipe substantially equal to the diameter of the circumscribed circle of the profiled part thereof.

Owing to the fact that the shaped and cylindrical portions of profile pipes manufactured in accordance with the disclosed method have substantially equal overall cross-sectional dimensions, a string of such profile pipes can be unobstructedly run into a well troublesome zone, so that after its reaming or expansion, it should reliably patch off this zone, tightly engaging the borehole wall.

The objects of the present invention are further attained by an apparatus capable of performing a method of manufacturing profile pipes, comprising a drawing bench having mounted thereon a drawing die accommodated in a housing and a drawing carriage, which apparatus, in accordance with the invention, further comprises cams situated in front of the drawing die at both sides of the path of the travel of a pipe being manufactured, the cams having deforming rollers mounted on their one ends and forked levers mounted on their other ends, operatively connected with the drawing carriage through a tie with slots receiving therein lock pins cooperating with the forked levers, and a pivoted lever with a bearing roller, mounted on the housing parallel with the path of the travel of the pipe being manufactured, one arm of the pivoted lever engaging a pipe being manufactured through the bearing roller and the other arm thereof carrying pivoted stops adapted for periodical cooperation with the cams.

The disclosed structure of the apparatus provides for reducing the number of production steps associated with the movement of the pipe for retracting therefrom the moulding device after the profiling of its central portion, and thus for simplifying, speeding up and economizing the process of making profile pipes with cylindrical ends, rendering this process continuous and automated, simplifying the task of the operating personnel and enhancing the overall productivity.

In its preferred embodiment, the apparatus according to the invention further comprises disks mounted on the common shafts with the cams, and double-arm levers having their one arms pivotally mounted on the housing and their other arms pivotally connected with the disks, the disks being operatively connected with the cams and the double-arm levers being operatively connected with the stops.

This structure of the apparatus reduces the load applied to the stops, thus prolonging their serviceability.

SUMMARY OF THE DRAWINGS

Other objects and advantages of the present invention will be made apparent in the following description of its embodiments, with reference being made to the accompanying drawings, wherein.

PREFERRED EMBODIMENT

The disclosed method of manufacturing profile pipes includes the following main steps.

A cylindrical pipe stock (blank) is drawn through a molding device, in which manner the central part only of the pipe is profiled and the pipe is reduced in diameter throughout its entire length, with the non-profiled cylindrical end portions of the pipe being reduced substantially to the diameter of the circumscribed circle of the profiled part of the pipe after the pipe has been drawn through the device the end portions of the pipe can be threaded, by means not included within the scope of this invention, for joining profile pipes into a string.

In cases where it is expedient to join certain pairs of profile pipes by welding, only one end portion is left cylindrical in the profiling of such pipes.

Figure 1:
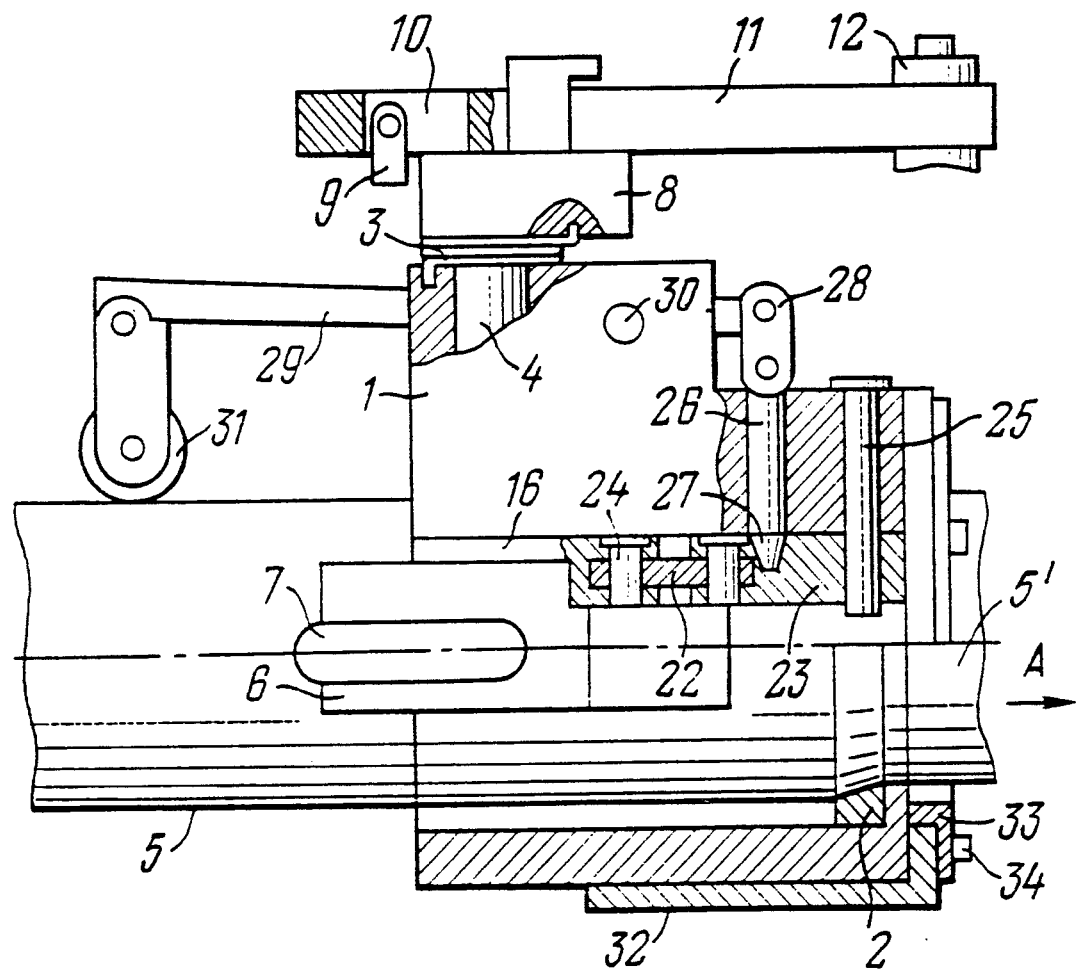
FIG. 1 is a general partly sectional view of an apparatus for performing the method of manufacturing profile pipes in accordance with the invention.
Figure 3:
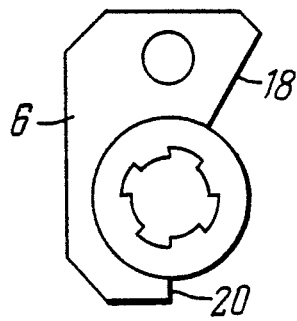
FIG. 3 is a view in plan of the cam of the apparatus of FIG. 1.
Figure 4:
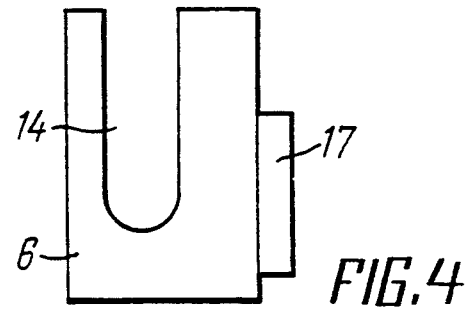
FIG. 4 is a side view of the cam of FIG. 3.
Figure 5:
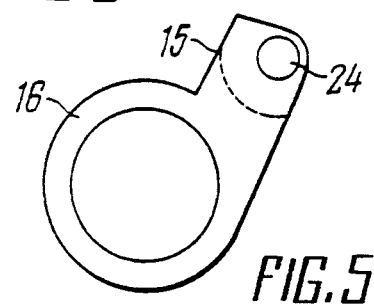
FIG. 5 is a view in plan of the disk of the apparatus of FIG. 1.
Figure 6:
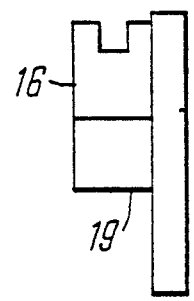
FIG. 6 is a side view of the disk of FIG. 5.
Figure 8:
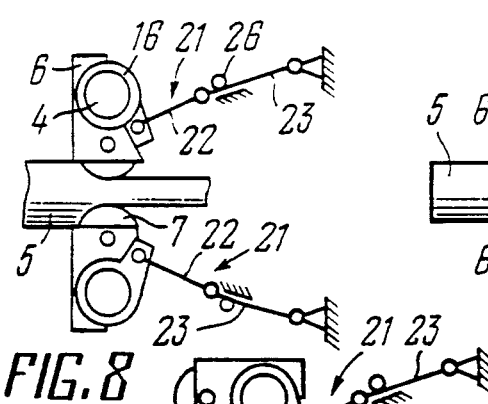
FIG. 8 schematically illustrates the mechanisms of FIG. 7 in their operating position.

The apparatus for performing the disclosed method comprises a housing 1 (FIG. 1) with a drawing die 2 mounted therein, and, urged by springs 3, shafts 4 vertically mounted in the housing 1 and having splines (not shown) cut in their end portions. The lower ends of the shafts 4 to both sides of the path of the travel of a cylindrical pipe blank 5 have mounted thereon cams 6 with deforming or shaping rollers 7, and the upper ends of the shafts 4 carry the respective forked levers 8, the latter being mounted for engagement with the respective lock pins 9 pivotally mounted in the slots 10 of a tie 11 mounted on the shaft 12 of the drawing carriage (not shown). The deforming rollers 7 are mounted on arbors 13 (FIG. 2) in the slots 14 (FIG. 4) of the respective cams 6 and are retained in their operating position by the abutments 15 (FIG. 5) of the projecting lugs of disks 16 mounted for rotation on cylindrical projections 16 (FIG. 4) of the cams 6 in engagement with the bearing surfaces 18 (FIG. 3), and in their idle position, in engagement of the thrust surfaces 19 (FIG. 6) of the disks 16 with the bearing surfaces 20 (FIG. 3) of the respective cams 6. The limiting of the angle of rotation of the disks 16 is effected by double-arm levers 21 composed of two arms or links 22 and 23 (FIGS. 1,2 and 8) pivotably joined to the housing 1 and to the respective disks 16 by means of pivots 24 and 25. The links 22 and 23 are restrained against pivoting by stops 26 in the form of rods with a tapering surface 27 (FIG. 1) at their lower end, mounted for vertical reciprocation in the housing 1. The stops 26 have their upper ends pivotally connected through shackles 28 to the respective one of the ends of a pivoted lever 29 which is mounted at its central portion on the housing 1 by means of a pivot 30, the other end of the pivoted lever 29 carrying a bearing roller 31. The lever 29 is pivotable relative to the housing 1 in a plane parallel with the longitudinal axis of the apparatus, the length of its arm at the side of the bearing roller 31 defining the length of the trailing cylindrical end portion of the pipe 5 engaged by the bearing roller 31. The apparatus is secured in advance to the rest 32 of the drawing bench (not shown) by means of a thrust ring 33 and bolts 34 (FIG. 1). In the initial position, the end of the pivoted lever 29 with the stops 26 is raised, and the effort of the spring 3 spreads the deforming rollers 7.

The apparatus is operated, as follows.

Figure 7:
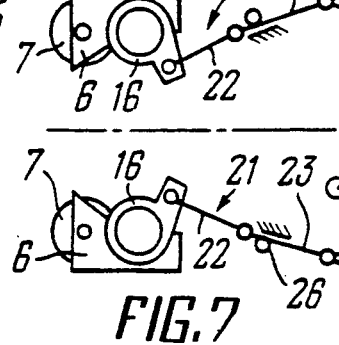
FIG. 7 illustrates schematically the double-link mechanisms with the disks and cams in the initial position prior to profiling the pipes.
Figure 10:
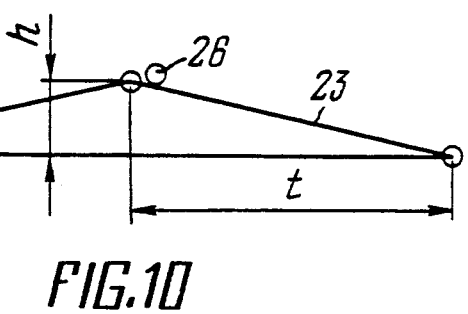
FIG. 10 illustrates schematically the relative positions of the arms of the double-link articulated mechanism.

A cylindrical pipe blank 5 to be profiled is introduced into the drawing die 2, its leading end having been prepared in advance (by complete reduction) for engagement by the drawing carriage (not shown). The engagement with the pipe blank 5 raises the bearing roller 31, as shown in FIG. 1, so that the other arm of the pivoted lever 29 with the stops 26 is lowered for abutment of the arms 23 against tapering ends 27 of the respective stops 26. The action of the spring 3 (FIG. 1) keeps the deforming rollers 7 spread, apart, as shown in FIGS. 2 and 7.

Figure 2:
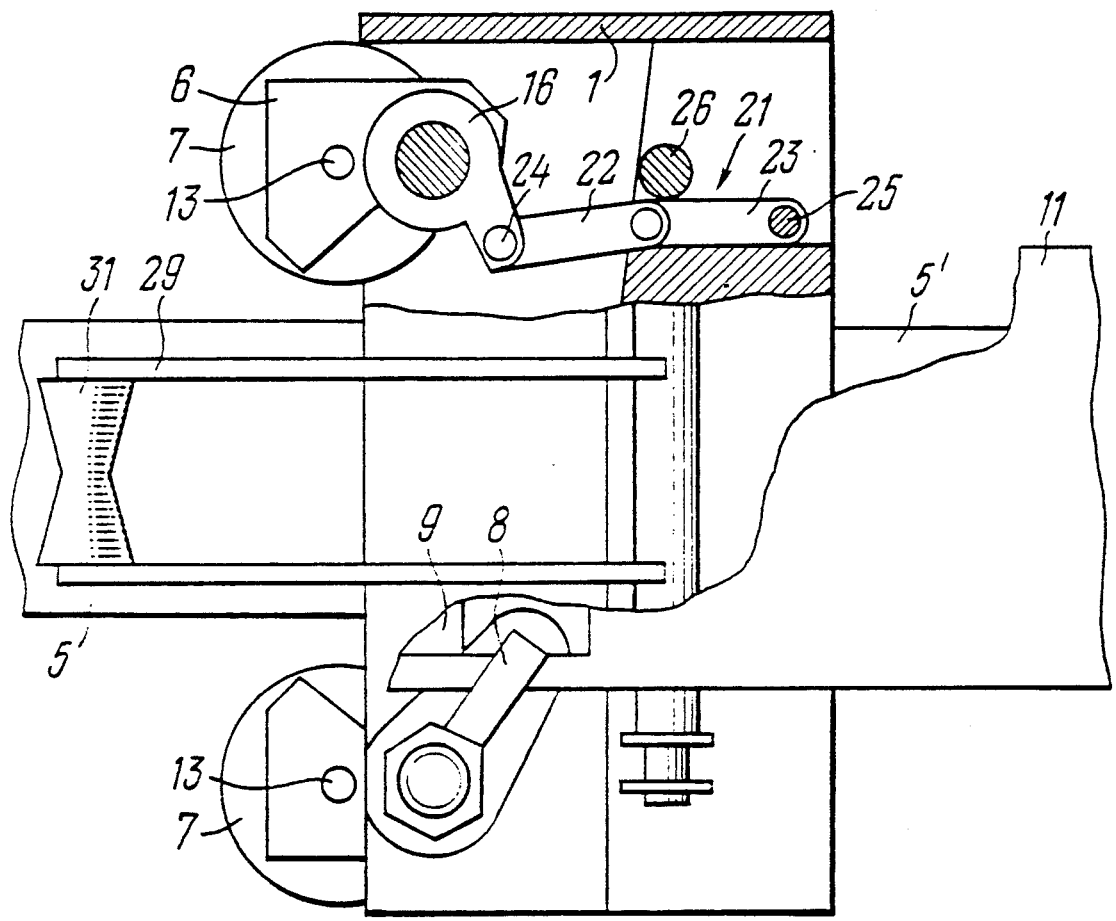
FIG. 2 is a view in plan of the apparatus of FIG. 1.

Then the drawing carriage (not shown) is run towards the apparatus from right to left in FIGS. 1 and 2 to engage the prepared leading end of the pipe blank 5, the advancing part of the tie 11 which mounts the lock pins 9 passing through the respective forked levers 8, with free backward pivoting of the lock pins 9, and being projected beyond the levers a predetermined length which defines the length of the leading cylindrical end portion 5' of the pipe 5 to be profiled. The ensuing working stroke of the drawing carriage from left to right (not shown) pulls the pipe blank 5 in the direction of arrow A in FIG. 1, the leading cylindrical end portion 5' of the pipe blank 5 passing through the drawing die 2 and being reduced to the required diameter. After the predetermined length of the leading cylindrical end portion 5' of the pipe blank 5 has been thus reduced, the lock pins 9 of the tie 11 engage the respective forked levers 8, turning them in the drawing direction, whereby the forked levers 8 turn correspondingly the respective shafts 4 with the cams 6 and their deforming rollers 7. The latter thus become pressed deformingly into the surface of the pipe blank 5 to an extent defined by the engagement of the bearing surface 18 (FIG. 3) of the cams 6 with the abutments 15 (FIG. 5) of the respective disks 16. This engagement retains the deforming rollers 7 (FIG. 8) in their operating position, as any rotation of the disks 16 in this position is opposed by the links 23 restrained from rotation (relative to the blank 5) by the respective stops 26, the tapering ends 27 (FIG. 1) of the stops 26 being thus subjected to a considerably lighter load than the profiling effort. With the forked levers 8 having rotated with their shafts 4 through an angle defining the required working position of the deforming rollers 7, they become disengaged from the respective lock pins 9 of the tie 11. The following displacement of the pipe blank 5 involves simultaneous profiling and reducing of the central portion of the pipe 5 by the drawing die 2, so that the diameter of the circumscribed circle of the profiled central part of the pipe 5 substantially equals the diameter of its leading cylindrical reduced end portion 5'.

Figure 9:
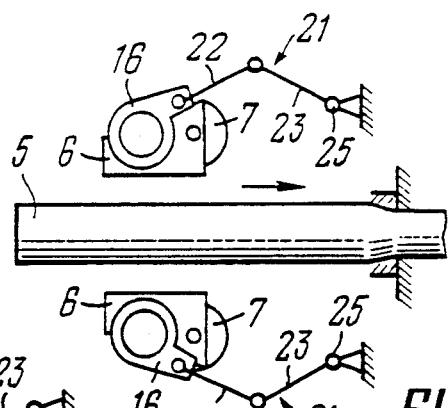
FIG. 9 schematically illustrates the mechanisms of FIG. 8 at the end of the pipe-profiling operation.

As the trailing end of the pipe blank 5 rides under the bearing roller 31, the latter plunges down under its own weight, disengaging the stops 26 from the respective links 23 which turn on their pivots 25 away from the pipe blank 5 (FIG. 9), with the cams 6 operatively connected with the links 22 through the respective disks 16 turning in the drawing direction, so that the profiling rollers 7 are withdrawn from the pipe blank 5. The unprofiled trailing cylindrical end portion of the pipe blank 5 passes through the drawing die 2 and becomes reduced substantially to the same diameter as its reduced leading cylindrical end portion 5' (FIG. 1). The springs 3 return the cams 6 with their rollers 7 into the initial position (FIG. 7).

This completes the process of the profiling of a pipe blank 5, combined with the process of its reduction.

INDUSTRIAL APPLICABILITY

The invention can be employed in the manufacture of profile pipes used for patching off troublesome zones in well-drilling and for repairs of well casings.

We claim:

1. An apparatus for manufacturing profile pipes of the type used in well construction, comprising a drawing bench having mounted thereon a drawing die (2) accommodated in a housing (1) and a drawing carriage, characterized in that it comprises cams (6) situated in front of the drawing die (2) at both sides of a path of travel of a pipe (5) being manufactured, the cams (6) having deforming rollers (7) mounted on their one ends and forked levers (8) mounted on their other ends, operatively connected with the drawing carriage through a tie (11) provided with slots (10) receiving therein lock pins (9) cooperating with the forked levers (8), and a pivoted lever (29) with a bearing roller (31), mounted on the housing (1) parallel with the path of travel of the pipe (5) being manufactured, one arm of the pivoted lever (29) engaging the pipe (5) being manufactured through the bearing roller (31), and the other arm thereof carrying pivoted stops (26) adapted for periodical cooperation with the cams (6).

2. An apparatus according to claim 1, characterized in that it comprises disks (16) mounted on common shafts with the cams (6), and double-arm levers (21) having their one arms (23) pivotally connected with the housing (1) and their other arms (22) pivotally connected with the disks (16), the disks (16) being operatively connected with the cams (6), and the double-arm levers (21) being operatively connected with the stops (26).

* * * * *